United States Patent [19]

Hollister et al.

[11] Patent Number: 5,073,164
[45] Date of Patent: Dec. 17, 1991

[54] SUCTION CATHETER

[76] Inventors: William H. Hollister, Box 458, E. Sullivan, N.H. 03445; Craig J. Bell, 27 Meadow Rd., E. Swanzey, Winchester, N.H. 03470; Cary D. Carruthers, 185 Boykerville Rd., Troy, N.H. 03465

[21] Appl. No.: 517,693

[22] Filed: May 2, 1990

[51] Int. Cl.⁵ ............................................ A61M 25/00
[52] U.S. Cl. ........................................ 604/43; 604/280
[58] Field of Search ............... 604/43, 44, 45, 171, 604/31, 280; 128/204.17, 207.14

[56] References Cited

U.S. PATENT DOCUMENTS

| | | | |
|---|---|---|---|
| 3,429,313 | 2/1969 | Romanelli | 604/31 |
| 3,628,532 | 12/1971 | Magrath | 128/204.17 |
| 3,991,762 | 11/1976 | Radford | 604/119 |
| 4,451,252 | 5/1984 | Martin | 604/43 |
| 4,776,841 | 10/1988 | Catalano | 604/43 |
| 4,881,542 | 11/1989 | Schmidt et al. | 128/207.14 |
| 4,995,865 | 2/1991 | Gahara et al. | 604/43 |

Primary Examiner—William H. Grieb
Attorney, Agent, or Firm—Pollock, Vande Sande & Priddy

[57] ABSTRACT

A suction catheter includes a multilumen catheter tube that contains a primary lumen for removing undesirable fluid from a patient upon application of a vacuum, and a secondary lumen contiguous with the primary lumen suitable for providing liquid to the interior of the primary lumen and to a patient; means for providing liquid to the interior of the secondary lumen; a patient connecting member; a vacuum connecting member; and a protective sleeve extending between the patient connecting member and the vacuum connecting member.

6 Claims, 2 Drawing Sheets

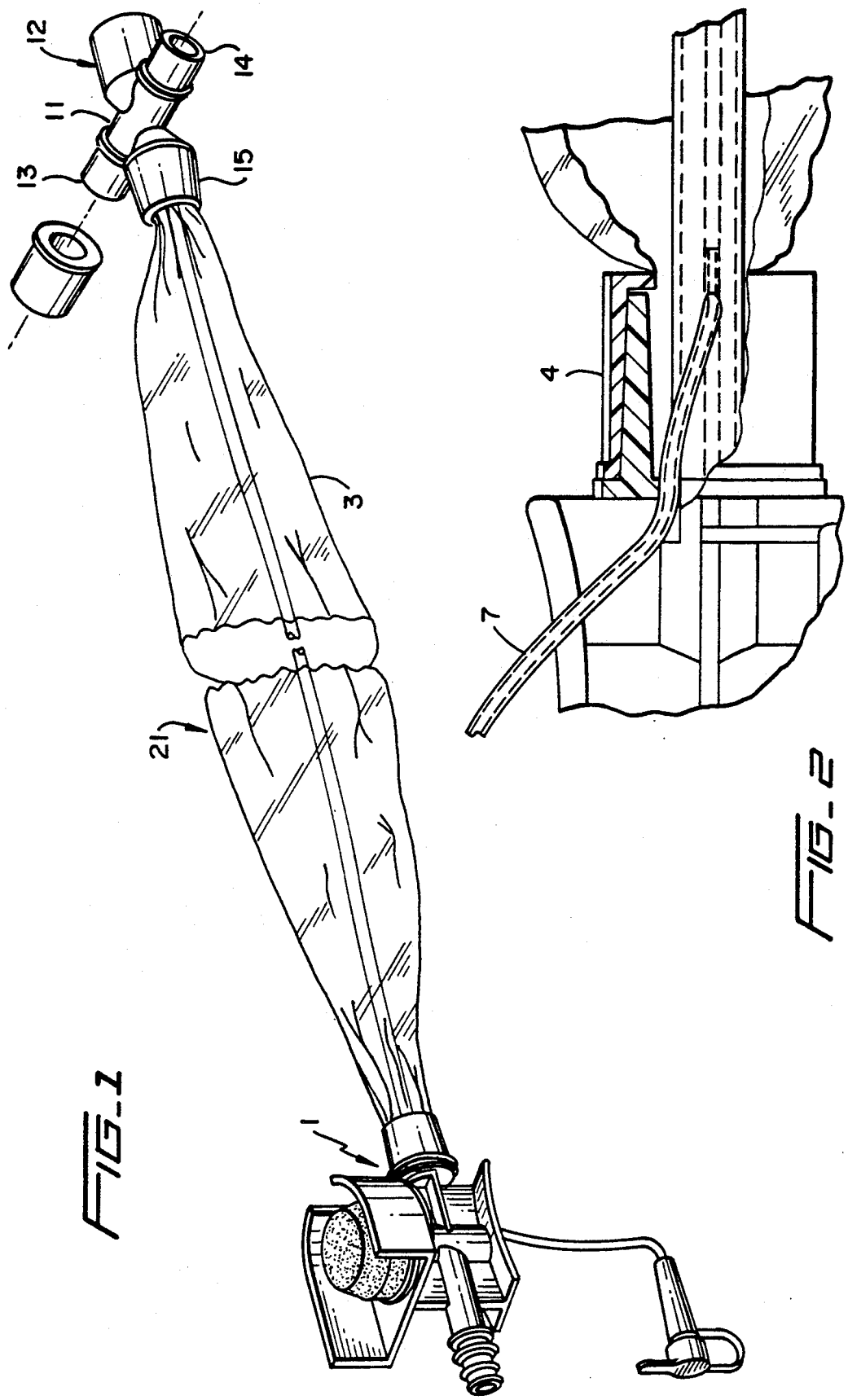

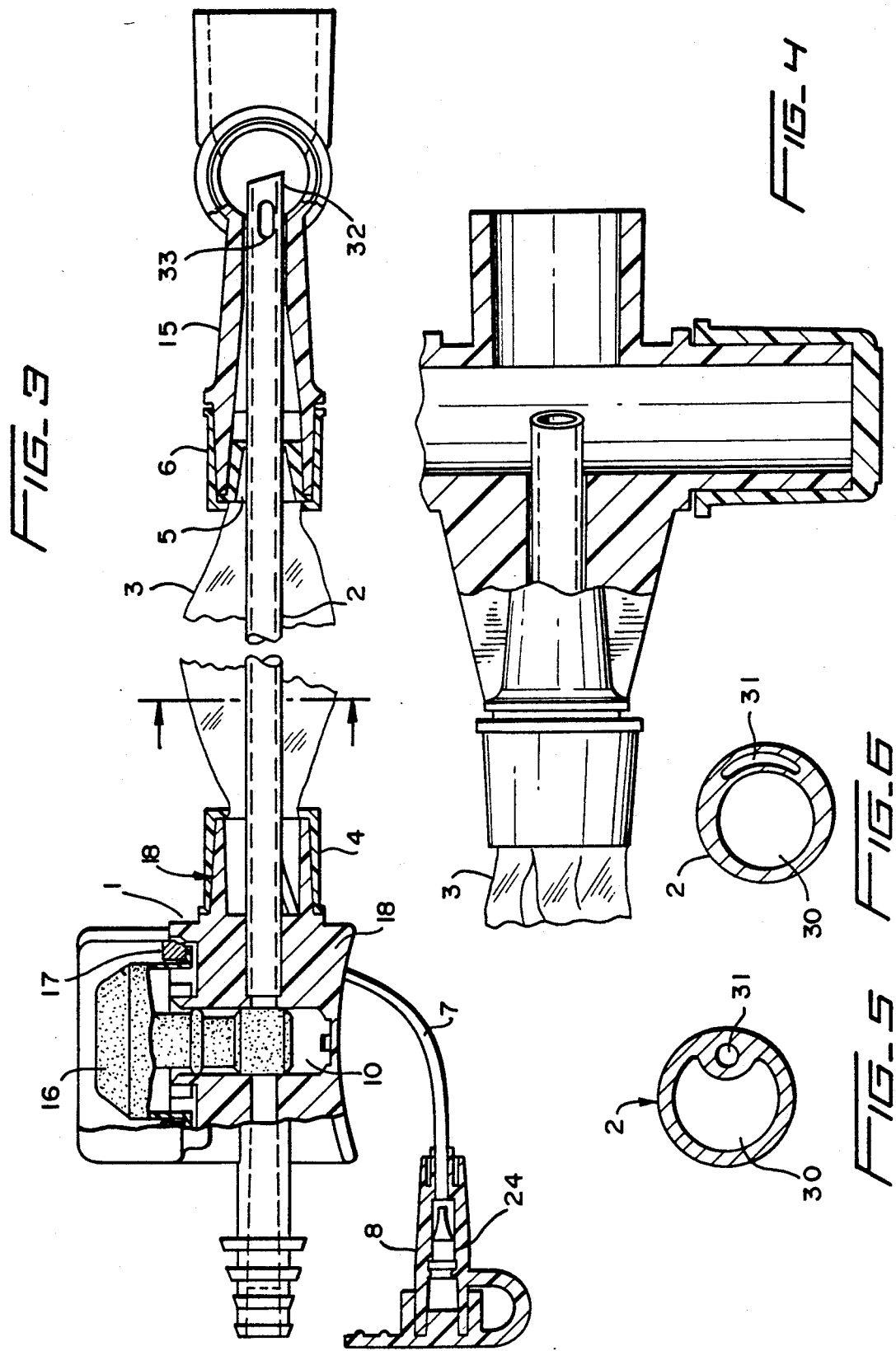

SUCTION CATHETER

DESCRIPTION

1. Technical Field

The present invention is concerned with a suction catheter suitable for use in removing undesirable fluid from a patient. In particular, the present invention is concerned with a suction catheter that includes a multilumen catheter tube whereby one of the lumens is suitable for supplying a fluid to the interior of the other lumen of the tube, for example, for irrigation purposes and to the patient for lavage purposes.

2. Background Art

A number of commercially available devices are currently in use for the purpose of ventilating a patient. Use of traditional endotracheal tubes for such purpose is quite satisfactory for ventilation purposes. However, during patient ventilation, frequently fluids accumulate in the trachea and bronchi. Commonly, mucous secretions and other fluids accumulate along the intubated pathway below and within the vicinity of, for instance, an inflated cuff, when employed. The patient may try to swallow the secretions, causing muscle contractions and tissue movement around the endotracheal tube, thereby contributing to the discomfort that is present during intubation. The accumulation of these fluids also can inhibit ventilation and increase the risk of infection. Accordingly, it is necessary for the accumulated fluids to be aspirated or suctioned from the patient.

In the past, suctioning has been achieved by removing the ventilation equipment thereby interrupting the patient's assisted ventilation, and inserting, such as into the trachea and bronchi, a catheter which in turn is connected to a vacuum source. After the fluid is removed via the catheter by application of the vacuum, the ventilation equipment is reattached to the patient and the ventilation is resumed.

However, this interruption of the patient's mechanically-assisted ventilation can cause extreme anxiety and discomfort. Also, it has been reported that during suctioning, oxygen desaturation can occur and may result in hypoxemia, brachcardia and other arrhythmias, a drop in blood pressure and possible increase in intracranial pressure. Also, it has been reported that during the suctioning, atelectasis or bronchoconstriction can also occur.

In order to eliminate or at least significantly minimize any of these problems, closed ventilation suction catheter systems are now in wide use such as that available under the trade designation of SteriCath, Model No. 6100 available from Smiths Industries Medical Systems, Inc. (SIMS), the assignee of the present application. This ventilation suction catheter system includes a catheter tube; a cross-piece connecting member for connection to an endotracheal tube and also for connection to a ventilating apparatus; a means for connecting a vacuum located at the end opposite to that nearest the patient; a control valve to control the suction; and a protective sleeve located between the cross-piece and the member for connecting to the vacuum.

Closed ventilation suction catheter systems make it possible to continue the ventilation while at the same time applying suction to remove undesired accumulated fluid from a patient.

In addition, in removing fluid from a patient, it sometimes becomes necessary to provide a lavage solution to the patient, especially when tenacious mucous has built up. To accomplish this, the Steri-Cath, Model No. 6100, catheter included a irrigation port located at the crosspiece whereby lavage solution could be conveyed to the catheter. In addition, irrigation solution could be provided which upon the application of vacuum would travel up through the interior of the catheter tube to help clean out areas within the tube containing occluded mucous or other materials that might block passage within the tube. Although, such device is quite satisfactory, improvement in the lavage and/or irrigation procedures would be desirable.

Provision of an irrigation port at a T-shaped connector for an entirely different purpose is also suggested in, for example, U.S. Pat. No. 3,991,762 to Radford, in which the irrigation port defines a passageway for allowing an irrigation fluid to flow about the exterior surface of the catheter tube as it is being withdrawn from the patient's trachea.

Also, certain dual lumen configurations have long been suggested for irrigating the interior of catheter tubes. See for example, U.S. Pat. Nos. 3,429,313 to Romanelli and 3,628,532 to Magrath.

SUMMARY OF INVENTION

The present invention is concerned with a suction catheter that makes it possible to more precisely administer a lavage solution to particular locations.

In particular, the present invention is concerned with a suction catheter that is suitable for use in removing undesirable fluid from a patient. The suction catheter comprises:

A. A multilumen catheter tube suitable for insertion into a patient wherein said catheter tube contains a primary lumen having an inside diameter suitable for removing fluid from a patient upon application of a vacuum, and a secondary lumen contiguous with said primary lumen having an inside diameter suitable for providing liquid for irrigation of the interior of said primary lumen or for lavaging said patient and being defined by an interior wall of said catheter tube and an exterior wall of said primary lumen, and wherein the ratio of the interior cross-sectional area of said secondary lumen to the interior cross-sectional area of said primary lumen being about 1:6 to about 1:8;

B. A patient connecting member mounted so as to surround said multilumen catheter tube in the vicinity of the distal end of said multilumen catheter tube, and wherein said distal end is suitable for insertion into a patient.

C. A vacuum connecting member located in the vicinity of the proximal end of the multilumen catheter tube.

D. A protective sleeve surrounding at least the majority of the length of said catheter tube and extending between said patient connecting member and said vacuum connecting member, wherein said protective sleeve is adapted to permit the distal end of said catheter tube to be extended from said protective sleeve into a patient and to be withdrawn from the patient.

E. Means for providing liquid to the interior of the said secondary lumen in the vicinity of the proximal end of said secondary lumen, including a connecting tube having one end connected and in communication with said secondary lumen inside said protective sleeve.

BRIEF DESCRIPTION OF THE DRAWINGS

FIG. 1 is an isometric view of the suction catheter assembly of the present invention;

FIG. 2 is a rear section view of valve assembly of FIG. 1 taken along lines II—II';

FIG. 3 is a cross-section view of the suction catheter assembly of FIG. 1 taken along lines III—III;

FIG. 4 is a partial section view of the cross-piece;

FIG. 5 is a section view of a double lumen suction catheter tube; and

FIG. 6 is a section view of a second embodiment of a double lumen suction catheter tube.

BEST AND VARIOUS FOR CARRYING OUT INVENTION

FIG. 1 is a perspective view of a suction catheter assembly 21 pursuant to the present invention. The suction catheter 21 can be connected through leg 12 of the cross-shaped piece 11 through a suitable connecting element to a patient, such as an oral and/or nasal connecting element and particularly an endotracheal or tracheostomy connector (not shown). The two legs of the cross-shaped piece, 13 and 14, are connected to ventilating apparatus (not shown) via an input tube (not shown) and a return tube (not shown) as known in the art. The remaining fourth leg 15 is affixed to the sleeve/collar assembly of the present invention. With respect to the discussion of the catheter of the present invention, the proximal ends of various elements are understood as the ends nearest the vacuum source (not shown) and the distal ends are understood to be those ends nearest the patient.

As best shown in FIGS. 1 and 3, the suction catheter of the present invention includes a multilumen catheter tube 2; a vacuum connection member 1; and a protective sleeve 3.

The multilumen catheter tube 2 is a soft flexible tube made of, for instance, polyvinylchloride, adapted to be inserted into a patient such as into the tracheo/bronchial tree of a patient for the purpose of removing fluid from the patient by employing vacuum. The multilumen catheter tube pursuant to the present invention includes at least one primary lumen 30 for removing undesirable fluid from the patient and a secondary and smaller interior lumen 31 contiguous with the first lumen for delivering liquid to the interior of the primary lumen, for example, for irrigation and/or lavage purposes. The secondary lumen can be integrally extruded with the primary lumen to produce the multilumen catheter tube employed pursuant to present invention. The structure of the catheter tube 2 with primary lumen 30 and interior lumen 31 is best shown in FIG. 5. FIG. 6 shows another design of lumens 30 and 31 of the catheter tube 2. According to preferred aspects of the present invention, the secondary lumen 31 referred to as the irrigation/lavage lumen has an interior cross-sectional area that is sized, with respect to the interior cross-sectional area of the primary suction lumen 30, such that resistance to the flow of fluid down the secondary lumen 31 is as low as possible and suction efficiency is as high as possible. The primary lumen has an interior cross-sectional area that is sufficient for efficiently removing undesirable fluid from the patient upon application of a vacuum.

According to preferred aspects of the present invention, such conditions are fulfilled by the structure in which the outside diameter of the multilumen catheter tube is approximately a 14 French units (FR) outside diameter tube. Typically, the outside diameter of the catheter tube is about 0.190 inches, the inside diameter is about 0.130-0.140 inches and the inside diameter of the secondary irrigation/lavage lumen is about 0.050 to about 0.055 inches. The wall thicknesses of the lumens are about $0.012 \pm 0.002$ inches. The interior cross-sectional area of the secondary lumen is typically about 0.00096 to about 0.002 $in^2$ and preferably about 0.001 to about 0.002 $in^2$. The interior cross-sectional area of the primary lumen is typically about 0.0132 to about 0.0154 $in^2$ and preferably about 0.0145 to about 0.0154 $in^2$. The ratio of the interior cross-sectional area of the secondary lumen to that of the primary lumen is typically about 1:6 to about 1:12, and preferably about 1:6 to about 1:8 and most preferably about 1:7.7. It is noted that although only two lumens have been described, if desired, the multilumen catheter tube of the present invention can contain three or more lumens for delivering other substances such as oxygen and/or medications.

The distal end 32 of the catheter tube 2 includes at least two peripheral cutout portions or eyes 33 through which body fluids can enter its interior when the catheter tube is located within a patient. Moreover, the body fluids can enter the catheter tube through its distal end 32 which is opened. The irrigation/lavage secondary lumen 31 terminates at its distal end at one of these holes present in the catheter tube. Such positioning of the distal end of the irrigation/lavage secondary lumen is very advantageous. This allows for any irrigation or lavage solution to come specifically out of the tip of the irrigation/lavage lumen at a precise predetermined location and makes it extremely easy to clear the catheter by instilling the irrigation/lavage solution while applying suction because the distal opening of the irrigation/lavage secondary lumen 31 is always in direct contact with the major or primary suction lumen 30.

The catheter tube, at its distal end, passes through the cross-shaped 11 piece through a wiper seal 5 located in the leg 15 of the cross-piece 11 and surrounding the periphery of the catheter tube. The wipe seal can be made of a silicone rubber material such as Verox 715 available from Elastomeric Products, Inc.

Located at the proximal end of the catheter tube is provided a means for connecting the catheter to a vacuum source, (not shown) referred to as vacuum connection member 1. Such includes a bore of the same size as the inside diameter of the suction catheter tube. The vacuum connection means is normally made of a relatively rigid material such as SAN (Polymer of Styrene and Acrylonitrile).

Also, located between the vacuum connection means 1 and the catheter tube 2 is a valve member 10. The valve member 10 illustrated is a spool type valve preferably made of butyl rubber. The valve is operated by manually applying a force to the top of the valve rubber member whereby the top of the rubber member and the valve member 10 is pushed down such that it no longer blocks the passageway in the catheter tube and thereby suction can be applied. Upon release of the manual force, the valve returns to its resting position. The rubber member 16 is ultrasonically welded to the valve body 18 of the valve member by a weld ring 17.

Located between the cross-piece 11 and the valve member 10 is a protective sleeve 3 that surrounds at least the majority of the length of the multilumen catheter tube. The protective sleeve 3 is adapted to permit the distal end of the multilumen catheter tube to be extended from the protective sleeve into a patient and to be withdrawn from the patient. The flexible protective sleeve is generally cylindrical in shape and is formed of a flexible, lightweight, translucent plastic material such as a high clarity polyethylene with a typical thickness of about 0.002 inches. The diameter of the protective sleeve is typically about 1.5 to about 1.7 inches and preferably about 2 inches ±0.31 inches when flattened.

The ends of sleeve 3 are adhesively secured to the leg 15 of the cross-piece 11 and leg 18 of the suction valve assembly 1, respectively, via collars 4 and 6. In assembling, the collars 4 and 6 are twisted and threaded over externally threaded legs 15 and 18 respectively, with the ends of the protective sleeve 3 and an adhesive located between the collars and the threaded legs. A typical adhesive is polyvinyl chloride doped tetrahydrofuran.

The irrigation/lavage liquid is brought into the catheter assembly in a novel and advantageous way. The structure of the present invention does not require any irrigation port in the cross-piece element 11 for providing irrigation fluid to the end of the suction catheter. Instead, the present invention includes a secondary lumen for providing liquid, such as irrigation lavage liquid to the interior of the primary lumen and/or to the patient, and means for providing this liquid to the secondary lumen. Means for providing liquid to the irrigation lavage secondary lumen include a connector tube 7 which has its one end bonded into the irrigation/lavage secondary lumen 32 by means of solvent bonding such as polyvinyl chloride doped tetrahydrofuran. This connection to the irrigation/lavage secondary lumen 31 is advantageously made inside the protective sleeve 3 to thereby keep movement of this connection to a minimum and to prevent it from breaking or leaking. Then, the connector tube 7 passes through the wall of the primary lumen, valve body, vacuum connection member 1 and has its other end bonded to a female luer fitting 8 which in turn is fitted with a sealable cap 9. The connection tube 7 is made of a plastic, such as polyvinyl chloride. Also, the female luer and sealable cap are likewise made of suitable plastic such as polyvinyl chloride.

Located inside female luer 8 is a one-way duckbill valve 24. The one-way duckbill valve serves the purpose of sealing against loss of ventilator air in the event the sealable cap is inadvertently left open. Loss of ventilator pressure would be detrimental to the patient. Moreover, the one-way valve is beneficial in that it will prevent mucous from being aspirated through the irrigation/lavage secondary lumen up to the unit dose vial when the unit dose vial is aspirating. This could occur if the unit dose vial of irrigation or lavage solution were attached to a connector that does not include a one-way valve. This would occur in such arrangement when the unit dose vial is squeezed and irrigation or lavage solution is expelled into the irrigation/lavage lumen. Upon removal of finger pressure, the unit dose vial will tend to return to its normal shape. In doing so, it will tend to suck in air, mucous or anything that tends to be near the distal tip of the irrigation/lavage lumen. The presence of the one-way duckbill valve in the connector in accordance with preferred aspects of the present invention is an assurance that such action will not suck in any mucous or undesirable substance into the unit dose vial which in turn could contaminate any further irrigation or lavaging. The sealable cap is provided with an interior protrusion so that a contact fit between the walls of the luer and inner walls of the female luer connection is provided.

While a preferred embodiment of the present invention has been illustrated and described, it will be appreciated that various changes can be made therein without departing from the spirit and scope of the present invention.

What is claimed is:

1. A suction catheter suitable for use in removing undesirable fluid from a patient, said suction catheter comprising:

a multilumen catheter tube suitable for insertion into a patient wherein said catheter tube contains a primary lumen having an inside diameter suitable for removing fluid from a patient upon application of a vacuum, and a secondary lumen contiguous with said lumen, having an inside diameter suitable for providing liquid for irrigation of the interior of said first lumen or for lavaging said patient and being defined by an interior wall of said catheter tube and an exterior wall of said primary lumen, the ratio of the interior cross-sectional area of said secondary lumen with respect to the interior cross-sectional area of said primary lumen being about 1:6 to about 1:8;

a patient connecting member mounted so as to surround said multilumen catheter tube in the vicinity of the distal end of said multilumen catheter tube, and wherein said distal end is suitable for insertion into a patient;

a vacuum connection member located in the vicinity of the proximal end of the multilumen catheter tube;

a protective sleeve surrounding at least the majority of the length of said catheter tube and extending between said patient connecting member and said vacuum connection member, wherein said protective sleeve is adapted to permit the distal end of said catheter tube to be extended from said protective sleeve into a patient and to be withdrawn from the patient; and means for providing liquid to the interior of the said secondary lumen in the vicinity of the proximal end of said secondary lumen including a connecting tube having one end connected and in communication with said secondary lumen inside said protective sleeve.

2. A suction catheter as claimed in claim 1, further including a valve located between said vacuum connection member and said catheter tube.

3. A suction catheter as claimed in claim 1, wherein said primary lumen includes at least two holes provided at a distal end thereof and wherein a distal end of said second lumen terminates above one of said holes.

4. A suction catheter as claimed in claim 2, wherein the other end of said connecting tube extends through said valve and is bonded to a female luer.

5. A suction catheter as claimed in claim 4, wherein said female luer is provided with a one-way duckbill valve.

6. A suction catheter as claimed in claim 1, wherein the ratio of the interior cross-sectional area of said secondary lumen with respect to the interior cross-sectional area of said primary lumen is about 1:7.7.

* * * * *